(12) United States Patent
Dolatkhani et al.

(10) Patent No.: US 11,318,044 B2
(45) Date of Patent: May 3, 2022

(54) AQUEOUS VISCOELASTIC SOLUTION AND USE THEREOF IN AN INJECTION DEVICE

(71) Applicant: POLYMEREXPERT SA, Pessac (FR)

(72) Inventors: Marc Dolatkhani, Cestas (FR); Anne Pagnoux, Le Barp (FR); Sonia Dakhli, Villenave d'Ornon (FR)

(73) Assignee: POLYMEREXPERT SA, Pessac (FR)

( * ) Notice: Subject to any disclaimer, the term of this patent is extended or adjusted under 35 U.S.C. 154(b) by 178 days.

(21) Appl. No.: 16/483,952

(22) PCT Filed: Feb. 9, 2018

(86) PCT No.: PCT/FR2018/050326
§ 371 (c)(1),
(2) Date: Aug. 6, 2019

(87) PCT Pub. No.: WO2018/146429
PCT Pub. Date: Aug. 16, 2018

(65) Prior Publication Data
US 2020/0046555 A1   Feb. 13, 2020

(30) Foreign Application Priority Data

Feb. 10, 2017 (FR) ..................................... 1751134

(51) Int. Cl.
| | | |
|---|---|---|
| *A61F 9/00* | (2006.01) | |
| *A61F 2/16* | (2006.01) | |
| *C10M 107/32* | (2006.01) | |
| *C10M 107/36* | (2006.01) | |
| *C10M 107/40* | (2006.01) | |
| *A61L 27/26* | (2006.01) | |
| *C08L 5/08* | (2006.01) | |
| *C08L 1/28* | (2006.01) | |

(52) U.S. Cl.
CPC .......... *A61F 9/0017* (2013.01); *A61F 2/1664* (2013.01); *A61F 2/1675* (2013.01); *A61L 27/26* (2013.01); *C08L 1/284* (2013.01); *C08L 5/08* (2013.01); *C10M 107/32* (2013.01); *C10M 107/36* (2013.01); *C10M 107/40* (2013.01); *C08L 2201/54* (2013.01)

(58) Field of Classification Search
None
See application file for complete search history.

(56) References Cited

U.S. PATENT DOCUMENTS

| | | | |
|---|---|---|---|
| 4,500,676 A * | 2/1985 | Balazs | A61L 27/26 |
| | | | 428/425.1 |
| 5,716,364 A | 2/1998 | Makker et al. | |
| 6,083,230 A | 7/2000 | Makker et al. | |
| 6,679,891 B2 | 1/2004 | Makker et al. | |
| 6,733,507 B2 | 5/2004 | McNicholas et al. | |
| 7,345,117 B1 * | 3/2008 | Barbucci | A61L 33/068 |
| | | | 525/454 |
| 2004/0241155 A1 | 12/2004 | Shah | |
| 2009/0060973 A1 | 3/2009 | Hunter et al. | |
| 2009/0118761 A1 | 5/2009 | Masters et al. | |
| 2016/0015865 A1 * | 1/2016 | Dolatkhani | C08G 18/10 |
| | | | 525/92 A |

FOREIGN PATENT DOCUMENTS

| | | |
|---|---|---|
| EP | 1496037 A1 | 1/2005 |
| EP | 1949871 A2 | 7/2008 |
| EP | 1992329 A1 | 11/2008 |
| JP | 3254752 B2 | 11/2001 |
| WO | 94/01468 A1 | 1/1994 |
| WO | 20100118080 A1 | 10/2010 |
| WO | 2013117863 A1 | 8/2013 |

OTHER PUBLICATIONS

International Search Report dated Apr. 3, 2018 for PCT/FR2018/050326 and English translation.

* cited by examiner

*Primary Examiner* — Jeffrey D Washville
(74) *Attorney, Agent, or Firm* — Lucas & Mercanti, LLP

(57) ABSTRACT

The invention relates to an aqueous viscoelastic solution comprising: at least one polymer selected from among hyaluronic acid and the salts thereof, and cellulosic derivatives and the salts thereof, in particular hydroxypropyl methylcellulose and the salts thereof; and at least one water-soluble polymer of the polyether-polyurethane or polyether-polyester-urethane type, and to the use thereof in a device intended for the injection of an intraocular implant.

19 Claims, No Drawings

AQUEOUS VISCOELASTIC SOLUTION AND USE THEREOF IN AN INJECTION DEVICE

CROSS REFERENCE TO RELATED APPLICATION

This Application is a 371 of PCT/FR2018/050326 filed on Feb. 9, 2018 which, in turn, claimed the priority of French Patent Application No. 1751134 filed on Feb. 10, 2017, both applications are incorporated herein by reference.

The invention relates to an aqueous viscoelastic solution comprising:
- at least one polymer selected from hyaluronic acid and derivatives thereof, such as one of the salts thereof, and the cellulosic derivatives and salts thereof, in particular hydroxypropyl methylcellulose and salts thereof, and
- at least one water-soluble polymer of the polyether polyurethane or polyether polyester urethane type, as well as use thereof in an injection device, in particular in a device intended for the injection of an intraocular implant.

The invention also relates to a device intended for the injection of an intraocular implant, comprising an injection body, a loading cartridge and an injection piston, in which the loading cartridge contains said aqueous viscoelastic solution.

Replacement of the crystalline lens of the eye affected by cataract is carried out with intraocular implants. Surgery using phacoemulsification allows the destruction of the natural crystalline lens and its elimination through a small incision. Implants made from flexible and pliable materials have been developed, capable of being inserted by means of injection devices through a micro-incision.

The injection system is composed of a tubular body in which the injection piston slides, surmounted by a cartridge for loading the ophthalmic implant and a conical tip the diameter of which reduces towards the injection end.

There are two types of injection devices used in ophthalmic surgery, commonly called "ophthalmic injectors":
- single-piece injector for which the cartridge for loading the implant and the tip are connected to the tubular body of the injector.
- injector constituted by two parts and for which the cartridge for loading the implant and the tip are separate from the tubular body. The two parts nest together after loading the implant into the cartridge (for example the Viscoject® system marketed by Medicel AG).

Regardless of the type of injector retained, the surgeon presses on the piston, the end of which pushes the implant that is located in the cartridge; the latter is increasingly stressed in the tip of the injector and finally exits the injector completely folded. It is thus possible to inject an implant of over 6 mm in diameter through an incision smaller than 3 mm. Very high stresses are thus exerted on the implant during the transfer. In order to limit the injection force and allow the implant to exit the tip undamaged, it is necessary on the one hand, to optimize the geometry of the injector, and on the other hand, to use a "lubricant".

The choice of material constituting the tip and the cartridge, as well as the optimization of the geometry thereof, are however insufficient for satisfactory injection of implants via micro-incisions. It is essential to use a lubricant allowing the implant to slide in the tip and the cartridge. The approaches allowing lubrication described in the literature are the use of a blooming agent and the utilization of a coating.

The first route relates to the use of a blooming agent incorporated by mixing (or "compounding" according to the usual term) into the thermoplastic polymer constituting the tip and the cartridge. This is generally an oleophilic or surface-active organic molecule of low molecular weight, containing 10 to 30 carbon atoms per molecule, derived from carboxylic acid and of glycerol monostearate (GMS), glycerol monopalmitate or also glycerol monooleate type etc. Placed in a mixture with polypropylene or polyamide, this type of molecule is distributed uniformly in the thermoplastic support just after injection and finally migrates to the surface of the support after several days or even several weeks. This blooming phenomenon is linked to the small size of the surface-active molecule, which is mobile compared to the macromolecular chains of the thermoplastic material.

By way of example, U.S. Pat. Nos. 6,733,507, 6,679,891 and 6,083,230 describe polypropylene (PP) cartridges containing a lubricant agent that migrates to the surface by the blooming phenomenon. This approach presents two major drawbacks.

The first is the presence of white marks on the injected implants. These are due to the fact that the blooming agent is not bound to the surface of the tip and is entrained during the injection. In fact, the blooming agents used are not water-soluble and their elimination is only possible after several rinses, once the implant has been injected.

The second drawback is linked to the kinetics of migration of the blooming agent to the surface of the support. This migration can take several days, or even several weeks, as a function of the conditions of implementation (injection-moulding of the part), the storage temperature, after-treatment, sterilization conditions, etc. before a sufficient quantity of lubricant is located at the surface of the injection cartridge. The quality of the lubrication will thus depend on the waiting time between the manufacture of the injector and the use thereof by the practitioner.

The non-reproducibility of the lubrication and the presence of whitish marks on the implants on injection represent the principal drawbacks of the use of these blooming agents.

A second approach ("coating" approach) allowing the implants to slide in the tips/cartridges of the injectors is the provision of a hydrophilic coating inside the tip. The lubrication principle consists of bulking the hydrophilic coating by the addition of a viscous product (solution of hyaluronate or of hydroxypropyl methylcellulose) and thus allowing sliding on a film of water formed at the interface.

The patents or patent applications JP56090838, JP3254752, U.S. Pat. No. 5,716,364, EP1949871, describe the possibility of producing a coating allowing the friction between the implant and the cartridge to be reduced or eliminated.

The hydrophilic coating is bound to the surface of the tip/cartridge either by covalent chemical bonds or by physical bonds.

With respect to the "coating" approach, the slippery properties are constant over time and do not evolve as in the case of the blooming agents. The major drawback of the methods consisting of coating the devices resides in the complexity of preparation of such coatings, in particular when the internal surface of the injectors is involved. This approach requires an operation in several steps: i) activating the surface ii), depositing the polymer film or polymerizing/grafting then iii) evaporating the solvent or the unreacted compound, finally iv) monitoring the characteristics of the film (homogeneity/thickness) etc. These procedures significantly increase the production time and the cost of access to devices having a slippery surface.

Regardless of the type of slip additive used (blooming agent of the GMS type or coating) at the level of the cartridge, the injection of the implant is carried out after addition of a viscoelastic solution (solution of hyaluronate or of hydroxypropyl methylcellulose).

It has now been found that the addition of a slip additive in the viscoelastic solution allows easy injection of the implant without any prior treatment of the cartridge of the injector. This approach overcomes the drawbacks of the existing approaches on the market, namely the non-reproducibility and the presence of marks on the cartridges compounded with blooming agents of the GMS type on the one hand, and on the other hand the high cost of the coatings prepared on the surface of the cartridges.

There is a great benefit in having available viscoelastic solutions making it possible on the one hand, for the implant to slide in the injector, and on the other hand, suitable for easy extraction at the end of the procedure.

According to data from the PMSI 2009 programme (Programme de Medicalisation des Systèmes d'Information), extracapsular extraction of the crystalline lens by phacoemulsification, with implantation of an artificial crystalline lens (intraocular lens) into the posterior chamber of the eye is the most frequent reason for hospital admission in France (over 98% of the reasons for admission).

This operation, broadly carried out in order to respond to cataract problems, requires an ocular incision that involves a loss of aqueous humour from the anterior segment of the eye. In order to rebalance the pressure of this segment, a viscoelastic solution is injected. It is characterized by a high viscosity that allows the volume of the eye to be maintained and also facilitates the surgical gestures of anterior capsular cutting (capsulorhexis). This viscous fluid thus ensures the protection of the corneal endothelium before the phacoemulsification phase (destruction of the crystalline lens by ultrasound and aspiration of the fragments), after which it will be evacuated.

During implantation of the lens, a fluid of lower viscosity is used in particular in the crystalline lens bag and/or in the ciliary sulcus in order to facilitate placement of the implant.

Several viscoelastic solutions for intraocular surgical use are commercially available. They are essentially composed of sodium hyaluronate (NaHA), combined or not with chondroitin sulfate or a cellulose derivative such as hydroxypropyl methylcellulose (HPMC). Such a solution is described, for example, in application US 2004/0241155.

The viscoelastic solutions based on sodium hyaluronate are differentiated by the origin of the hyaluronic add, the molecular weight (between 0.22 MDa and 6 MDa) and the viscosity at rest (between 10 Pa·s and 7,000 Pa·s) (source: Les solutions viscoélastigues, CHIRURGIE DE LA CATARACTE, Cahier des dispositifs médicaux Le Moniteur Hospitaller No. 259 of Jan. 10, 2013).

There is another category of viscoelastic solution, based on hydroxylpropyl methylcellulose (HPMC) or hypromellose, of plant origin. Hypromellose is characterized by the spreading capacity thereof and therefore the ability thereof for protection of the endothelium. It has a low viscosity. The extraction thereof at the end of the procedure is more difficult.

Application EP 1496037 describes a product for the modification of hyaluronic acid, in which hyaluronic acid or one of its pharmaceutically acceptable salts is combined with a block polymer. This modification product can be used as a therapeutic product in ophthalmic or reconstructive surgery, or also for the treatment of joint disorders.

The viscoelastic solutions according to the invention are viscoelastic solutions for intraocular surgical use, the specificity of which is to have physicochemical properties allowing the implant to slide in the injector, i.e. a mechanical action and not a therapeutic one. This property is based on the composition of the solution, the principal ingredient of which is a polymer selected from hyaluronic acid and salts thereof, sodium hyaluronate being preferred, and cellulosic derivatives, in particular hydroxypropyl methylcellulose and salts thereof, with which is combined, preferably in a small quantity, a water-soluble polymer of the polyether urethane or polyether polyester urethane type, having intrinsic lubrication properties in an aqueous medium.

Said polymer selected from hyaluronic acid and salts thereof, sodium hyaluronate being preferred, and the cellulosic derivatives and salts thereof (in particular hydroxypropyl methylcellulose and salts thereof) is preferably present in the aqueous viscoelastic solution in a much larger quantity than that of the water-soluble polymer of the polyether polyurethane or polyether polyester urethane type.

By "salt" is meant in the present description a pharmaceutically acceptable salt.

The behaviour of the highly pseudoplastic viscoelastic solutions, i.e. those the viscosity of which reduces under shear, used according to the invention allows both easier placement of the implant and easy removal of the viscous solution during the surgical operation, which gives them a significant advantage with respect to the existing viscoelastic solutions. This advantage is contributed by the slippery property conferred by the water-soluble polymer contained in the solution. The slipperiness can be quantified by measuring the force necessary for the injection of the intraocular lens.

The viscoelastic solutions according to the invention are sterile, non-immunogenic, non-toxic solutions, close to the physiological pH of the eye (6.8-7.6), transparent, easy to inject and to remove.

Depending on the molecular weight of the polymer selected from hyaluronic acid and salts thereof and the cellulosic derivatives, in particular hydroxypropyl methylcellulose and salts thereof, the viscoelastic solutions will be either of the cohesive type, or the dispersive type, for sequential or joint use.

By way of example, the viscoelastic solutions of the cohesive type can comprise hyaluronic acid of molecular weight comprised between 1.5 Mda and 5 MDa. By "molecular weight" is meant the weight average molecular weight (Mw). Alternatively, the viscoelastic solutions of the dispersive type can contain hyaluronic acid of lower molecular weight, comprised between 0.5 Mda and 1.5 MDa. The viscoelastic solutions can, for example, contain up to 0.5%, in particular 0.25% (expressed in weight/volume) of slippery polymer (water-soluble polymer of the polyether urethane or polyether polyester urethane type) and are constituted by isotonic solutions ensuring a physiological pH and an osmolality of 300 to 350 mOsm/kg.

A subject of the invention is therefore an aqueous viscoelastic solution comprising:

at least one polymer selected from hyaluronic acid and salts thereof, and cellulosic derivatives and salts thereof, and at least one water-soluble polymer of the polyether polyurethane or polyether polyester urethane type.

Advantageously, the aqueous viscoelastic solution according to the invention is in the form of a gel and in particular has a viscosity comprised between 10 and 7000 Pa·s, in particular between 30 and 1000 Pa·s, more particularly between 50 and 200 Pa·s.

It will be noted that in the present description, and unless specified to the contrary, the value ranges indicated are understood to be inclusive.

The viscosity can be measured according to the usual methods in the field, for example by rheology measurement in flow using a rheometer (for example trade name TA and type AR 1000), The curve of viscosity as a function of shear allows the value for viscosity at zero shear to be obtained.

Said water-soluble polymer of the polyether polyurethane or polyether polyester urethane type present in the composition according to the invention does not have a terminal or pendant fatty acid chain comprising at least 10 carbon atoms.

Preferably, the hyaluronic acid can have a weight average molecular weight comprised between 1.5 MDa and 5 MDa, or alternatively, comprised between 0.5 MDa and 1.5 MDa.

Preferably, the hyaluronic acid is in the form of a salt, preferably sodium or potassium hyaluronate.

A preferred cellulosic derivative for the purposes of the invention is hydroxypropyl methylcellulose or one of the salts thereof, in particular sodium or potassium salt.

Preferably, the content of polymer selected from hyaluronic acid and/or one of the salts thereof and the cellulosic derivatives, in particular hydroxypropyl methylcellulose, and/or one of the salts thereof, in the aqueous viscoelastic solution can be comprised between 0.5 and 3%, preferably between 1 and 2.5%, expressed in weight/volume or, in other words, between 5 mg/mL and 30 mg/mL.

Preferably, hyaluronic acid and/or one of the salts thereof, on the one hand, and the cellulosic derivative, in particular hydroxypropyl methylcellulose and/or one of the salts thereof, on the other hand, are present in said viscoelastic solution at the rate of 5 to 25 mg/mL, in particular from 10 to 25 mg/mL.

Water-soluble thermogelling polymers of the polyether polyurethane type that are particularly suitable for use according to the invention are poly(urea-urethane)s comprising poly(ethylene oxide-b-propylene oxide-b-ethylene oxide) (PEO-b-PPO-b-PEO) groups, in particular branched ethylene oxide and propylene oxide block copolymers comprising urethane, allophanate and urea bridges such as those described in application WO03106536.

These poly(urea-urethane)s are obtained by polycondensation of diisocyanates and thermosensitive (PEO-b-PPO-b-PEO) triblock diols and can comprise urethane and/or allophanate groups, urea and/or biuret. These polymers are known in particular as ExpertGel® and marketed by the company PolymerExpert.

These water-soluble thermogelling polymers of the polyether polyurethane type preferably have a weight average molecular weight greater than or equal to 20 KDa, and more particularly, a molecular weight comprised between 20 and 100 KDa.

The water-soluble polyether polyester urethane type polymer can be a branched polyether and polyester copolymer comprising urethane, allophanate and urea bridges. These copolymers preferably have a weight average molecular weight greater than or equal to 20 KDa, and in particular, comprised between 20 and 100 KDa. These polyether-polyester-urethanes are obtained by polycondensation of diisocyanates and polyether and polyester diols and can comprise urethane and/or allophanate groups, urea and/or biuret.

The water-soluble polymer content of polyether polyurethane or polyether polyester urethane type in the aqueous viscoelastic solution can be comprised between 0.10 and 0.5%, preferably between 0.10 and 0.25%, expressed as weight/volume or, in other words, between 1 mg/mL and 5 mg/m L, preferably between 1 mg/mL and 2.5 mg/mL.

Another subject of the invention is the use of an aqueous viscoelastic solution as described above, comprising:
at least one polymer selected from hyaluronic acid and salts thereof, and cellulosic derivatives and salts thereof, and
at least one water-soluble polymer of the polyether polyurethane or polyether polyester urethane type,
in an injection device.

Another subject of the invention is a viscoelastic solution as described above, for use thereof for the injection of a hydrophilic or hydrophobic intraocular implant.

All the general or particular aspects of said aqueous viscoelastic solution, mentioned in the present description, are applicable to these uses.

Advantageously, the use of said aqueous viscoelastic solution makes it possible to reduce the force to be exerted on the piston of said injection device, commonly called "injection force".

According to a preferred aspect, said injection device can be a device intended for the injection of an intraocular implant (commonly called "ophthalmic injector").

Said viscoelastic solution acts as a slip additive, but without coating the surface of the cartridge of the injector.

The device intended for the injection of an intraocular implant can comprise, in particular, an injection body, a tip, a loading cartridge and an injection piston.

According to an advantageous aspect, the viscoelastic solution as described above can be introduced into said loading cartridge and into the tip before, or simultaneously with, the loading of the intraocular implant. Advantageously, said viscoelastic solution allows the injection of a hydrophilic or hydrophobic intraocular implant by an injection device equipped with a tip having an aperture of diameter equal to or less than 2.6 mm with an injection force less than 30 N, preferably less than 25 N. According to the invention, this result is obtained even though the loading cartridge has not undergone any treatment of the "coating" type and no blooming agent has been incorporated into the thermoplastic polymer constituting the tip.

The invention also relates to a device intended for the injection of an intraocular implant, comprising an injection body, a loading cartridge and an injection piston, in which the loading cartridge contains a viscoelastic solution as defined above, in all the general and preferred aspects thereof.

The invention is illustrated by the examples below. Examples 1 to 4 relate to the preparation of water-soluble polymers of the polyether urethane and polyether polyester urethane type that can be used for the purposes of the invention and Examples 5 to 8 relate to viscoelastic solutions according to the invention and the study of the properties thereof.

The following abbreviations are used:
GMS: glycerol monostearate
NaHA: sodium hyaluronate
HPMC: hydroxypropyl methylcellulose
PEG: polyethylene glycol Example 1: Preparation of a Water-Soluble Polymer of the Polyether Polyurethane Type (EG230)

The EG230 polymer is a polyurethane composed of a triblock ethylene oxide-propylene oxide-ethylene oxide copolymer linked together by urethane, allophanate and urea bonds. The EG230 polymer is obtained by reaction between the polymers having hydroxyl groups and an isocyanate reagent.

ADEKA NOL F-108 is dried in a reactor under vacuum and under continuous stirring at 120° C. so that all of the water is removed. PEG 600 is placed in a heatproof, vacuum-proof vessel and left to melt under vacuum at 80° C. until melting is complete.

After cooling the reactor containing the F-108 to a temperature of approximately 70° C., the 2-butanone previously dried over $CaCl_2$ and filtered is added under nitrogen, then water, dicyclohexylmethane 4,4'-diisodicyanate and tin dibutyl dilaurate (catalyst). The reagents are mixed while maintaining the heating.

When the conversion of the isocyanate functions reaches 58%, the dry, liquid PEG 600 (80° C.) is added in one go under a nitrogen stream. The heating is stopped when at least 99% of the isocyanates are consumed.

After stopping the nitrogen stream, ethanol is added to the reaction medium under stirring during 30 min. The EG230 polymer is precipitated from 1.5 times the volume of reaction medium and dried at 40° C. under vacuum.

The composition thereof is given in Table 1 below:

TABLE 1

| | Molar Ratio | Molecular Weight (g/mol) | Weight (g) |
|---|---|---|---|
| ADEKA NOL F-108 (marketed by ADEKA) | 1 | — | 300 |
| Dicyclohexylmethane 4,4'-diisocyanate | 2.06 | 262 | 15 |
| polyethylene glycol (PEG 600) monomethyl ether | 1.73 | 600 | 35 |
| Dry 2-butanone | — | | 900 mL |
| Demineralized water | 0.2 g/100 g F-108 | | 0.6 |
| Tin dibutyl dilaurate | 500 ppm/ F-108 | | 0.15 |
| Ethanol 99% undenatured | 100 mL/100 kg F-108 | | 100 mL |

Example 2: Preparation of a Water-Soluble Polymer of the Polyether Polyurethane Type (EG68(0))

ExpertGel EG68(0) is a polyurethane composed of a triblock ethylene oxide-propylene oxide-ethylene oxide copolymer linked together by urethane, allophanate and urea bonds. ExpertGel EG68(0) is obtained by reaction between the polymers representing hydroxyl groups and an isocyanate reagent.

Briefly, Lutrol F68 (Kolliphor P188) is dried in a reactor under vacuum and under continuous stirring at 120° C. so that all of the water is removed. The PEG 600 is placed in a heatproof and vacuum-proof vessel and left to melt under vacuum at 80° C. until melting is complete.

After cooling of the reactor containing the F68 to a temperature of approximately 70° C., the 2-butanone previously dried over $CaCl_2$) and filtered is added under nitrogen, then water, dicyclohexylmethane 4,4'-diisodicyanate and tin dibutyl dilaurate (catalyst). The reagents are mixed while maintaining the heating.

When the conversion of the isocyanate functions reaches 58%, the dry, liquid PEG 600 (80° C.) is added in one go under a nitrogen stream. The heating is stopped when at least 99% of the isocyanates are consumed.

After stopping the nitrogen stream, ethanol is added to the reaction medium under stirring during 30 min. The EG68(0) polymer is precipitated from 1.5 times the volume of reaction medium and dried at 40° C. under vacuum.

The composition thereof is given in Table 2 below:

TABLE 2

| | Molar Ratio | Molecular Weight (g/mol) | Weight (g) |
|---|---|---|---|
| Lutrol F68 (Kolliphor P188 marketed by BASF) | 1 | — | 300 ± 3 |
| Dicyclohexylmethane-4,4' diisocyanate | 2.06 | 262 | 18.4 |
| Polyethylene glycol (PEG 600) monomethyl ether | 1.82 | 600 | 37.1 |
| Tin dibutyl dilaurate | 500 ppm/ F68 | | 0.15 |
| Dry 2-butanone | — | | 0.9 L |
| Demineralized water | 0.2 g/100 g F68 | | 0.6 |
| Ethanol 99% undenatured | 5 mL/kg F68 | | 0.15 |

Example 3: Preparation of a Water-Soluble Polymer of the Polyether Polyurethane Type (EG88(0))

The EG88(0) polymer is a polyurethane composed of a triblock ethylene oxide-propylene oxide-ethylene oxide copolymer linked together by urethane, allophanate and urea bonds. The EG88(0) polymer is obtained by reaction between the polymers representing hydroxyl groups and an isocyanate reagent. The synthesis protocol is similar to that of the EG68(0) polymer in Example 2, but replacing Lutrol F68 with Lutrol F88.

The composition thereof is given in Table 3 below:

TABLE 3

| | Molar Ratio | Molecular Weight (g/mol) | Weight (g) |
|---|---|---|---|
| Lutrol F88 (marketed by BASF) | 1 | — | 300 ± 3 |
| Dicyclohexylmethane-4,4' diisocyanate | 2.06 | 262 | 14.2 |
| Polyethylene glycol (PEG 600) monomethyl ether | 1.82 | 600 | 28.7 |
| Tin dibutyl dilaurate | 500 ppm/ F88 | | 0.15 |
| Dry 2-butanone | — | | 0.9 L |
| Demineralized water | 0.2 g/100 g F88 | | 0.6 |
| Ethanol 99% undenatured | 5 mL/kg F88 | | 0.15 |

Example 4: Preparation of a Water-Soluble Polymer of the Polyether Polyester Urethane Type (ES)

The ES polymer is a branched polyether and polyester copolymer having urethane and allophanate bridges (and very little urea). It is obtained by reaction of a dihydroxytelechelic polycaprolactone and a polyethylene glycol and a diisocyanate.

Briefly, the polycaprolactone (CAPA) and the PEG are dried in a reactor under vacuum and under continuous stirring at 100° C. When the CAPA and the PEG are completely melted, the heating and the vacuum are maintained, so that all of the water contained in the polymers is removed.

After cooling the reactor to a temperature of approximately 80° C., the 2-butanone previously dried over $CaCl_2$ and filtered is added under nitrogen, then dicyclohexylmethane 4,4' diisocyanate and bismuth carboxylate (catalyst). The reagents are mixed while maintaining the heating for at least 15 h at 60° C.

After stopping the nitrogen stream, ethanol is added to the reaction medium under stirring during 30 min, then the absence of isocyanate is verified. The reaction medium is diluted with 17 L of 2-butanone, then the final ES polymer is precipitated from heptane and dried at 40° C. under vacuum.

The composition thereof is given in Table 4 below:

TABLE 4

|  | Weight (g) |
| --- | --- |
| Polycaprolactone CAPA 2125 (marketed by Perstorp) | 305.5 |
| Polyethylene glycol (PEG 6000) monomethyl ether | 6700 |
| Dicyclohexylmethane-4,4' diisocyanate | 329.2 |
| Bismuth carboxylate | 3.5 |
| Dry 2-butanone | 3.08 L |
| Ethanol 99% pure | 10 mL |

Example 5: Preparation of an Aqueous Viscoelastic Solution Comprising a Water-Soluble Polymer of the Polyether Polyurethane or Polyether Polyester Urethane Type with 0.25% Weight/Volume The first part of the preparation is carried out in a clean room. A 2.5% weight/volume solution of water-soluble polymer of polyether urethane type such as those indicated in Examples 1 to 3 or polyether polyester urethane such as the one in Example 4 is produced by dissolution under mechanical stirring by introducing the polymer (2.5 g) in powder form into isotonic water buffered at pH 7 (97.5 mL). After complete dissolution, the solution is sterilized by filtration at 0.2 microns on a nylon filter. Sodium hyaluronate is added (16 g) in powder form to the polymer solution and 884 mL of buffered isotonic water is added in order to adjust the concentrations. The mixture is shaken on an orbital mixer at a speed of 300 rpm at ambient temperature until complete dissolution of the sodium hyaluronate.

After approximately 30 h of solubilization, the aqueous viscoelastic solution comprising 16 mg/mL of sodium hyaluronate (1.6%) and 2.5 mg/mL water-soluble polymer of polyether polyurethane or polyether polyester urethane (0.25%) type is placed in the syringe.

Example 6: Packaging of the Aqueous Viscoelastic Solutions Comprising Sodium Hyaluronate and a Water-Soluble Polymer of the Polyether Polyurethane or Polyether Polyester Urethane Type The pre-sterilized syringes are filled with 1.1 mL of solution. They are then sterilized in an autoclave.

The secondary wrapping in a polyester blister pack is then carried out before proceeding to a fresh sterilization by ethylene oxide (ETO).

Example 7: Aqueous Viscoelastic Solutions Comprising a Water-Soluble Polymer of the Polyether Polyurethane Type and Sodium Hyaluronate (NaHA)

Different aqueous viscoelastic solutions according to the invention and the characteristics thereof are given in Table 5 below.

TABLE 5

| Polymer in the solution | HA concentration | Polymer concentration | HA Molar Weight | Viscosity* (Pa · s) |
| --- | --- | --- | --- | --- |
| EG230 0.25% | 16 mg/mL | 2.5 mg/mL | 1.9 MDa | 130 |
| EG230 0.1% | 16 mg/mL | 1.0 mg/mL | 1.9 MDa | 110 |
| EG88(0) 0.25% | 16 mg/mL | 2.5 mg/mL | 1.9 MDa | 135 |
| EG88(0) 0.1% | 16 mg/mL | 1.0 mg/mL | 1.9 MDa | 110 |
| EG68(0) 0.25% | 16 mg/mL | 2.5 mg/mL | 1.9 MDa | 90 |
| EG68(0) 0.1% | 16 mg/mL | 1.0 mg/mL | 1.9 MDa | 100 |

*at a zero shear rate determined by a TA rheometer of the AR1500EX type, aluminium cone-and-plate geometry, 40 mm, 63 μm, 2°, T = 25° C.

Example 8: Tests of the Injection of Intraocular Lenses (IoI) in the Presence of Aqueous Viscoelastic Solutions Comprising a Water-Soluble Polymer of the Polyether Polyurethane or Polyether Polyester Urethane Type The tests were carried out with certain viscoelastic solutions of Example 7, by using cartridges without any treatment promoting the ejection of the lens (no coating or GMS).

The following procedure was followed:

An ophthalmic implant was introduced into the loading cartridge of an injection system comprising an injection body, a loading cartridge (that has not undergone any treatment of the coating or GMS type) and an injection piston.

A viscoelastic solution according to the invention is added thereto, namely a solution of NaHA or HPMC combined with a polymer allowing slipperiness in said loading cartridge. The injection system is placed in a dynamometer of the Instron 3367 type equipped with a force sensor of 0.5 kN sensitivity, at a compression velocity of 8.5 mm/s. The compression force necessary for the injection of the implant is measured, in comparison with a viscoelastic solution on the market containing only NaHA (Visthesia® solution marketed by Zeiss) or a viscoelastic solution containing HMPC only.

The results are given in Tables 6 and 7 below.

1) Injection of a hydrophilic intraocuiar lens (IOL) through a non-coated Viscoject tip of inside diameter 2.0 mm (commercial IOL AcriLISA® from Zeiss)

TABLE 6

| Nature of the viscoelastic solution | Injection force (N) | |
| --- | --- | --- |
|  | 17 dioptres | 28 dioptres |
| NaHA 1.6%-EG88(0) 0.25% | 11 +/− 1 | 12 +/− 1 |
| NaHA 1.6%-EG88(0) 0.10% | 12 +/− 2 | 14 +/− 1 |
| NaHA 1.6%-EG230 0.25% | 13 +/− 2 | 12 +/− 0 |

TABLE 6-continued

| Nature of the viscoelastic solution | Injection force (N) | |
|---|---|---|
| | 17 dioptres | 28 dioptres |
| NaHA 1.6%-EG230 0.10% | 13 +/− 2 | 12 +/− 0 |
| NaHA 1.6%-EG68(0) 0.25% | — | 12 +/− 0* |
| NaHA 1.6%-EG68(0) 0.10% | — | 12 +/− 1* |
| NaHA 1.6%-ES 0.25% | 10 +/− 0 | 13 +/− 3 |
| NaHA 1.6%-ES 0.10% | 14 +/− 2 | 17 +/− 1 |
| Visthesia ® solution (Zeiss) | Not ejected | Not ejected |
| HPMC* 1.5%-EG68(0) 0.25% | 16 +/− 1 | 18 +/− 2 |
| HPMC* 1.5% | Not ejected | Not ejected |

*HPMC of molar weight 800 KDa

2) Injection of a hydrophobic intraocular lens (IOL) through a non-coated Viscoject tip of inside diameter 2.6 mm (commercial IOL Hydromax® from Zeiss)

TABLE 7

| Nature of the viscoelastic solution | Injection force (N) | |
|---|---|---|
| | 11 dioptres | 28 dioptres |
| NaHA 1.6%-EG88(0) 0.25% | 18 +/− 4 | 27 +/− 0 |
| NaHA 1.6%-EG88(0) 0.10% | 16 +/− 1 | 28 +/− 1 |
| NaHA 1.6%-EG230 0.25% | 15 +/− 3 | 21 +/− 3 |
| NaHA 1.6%-EG230 0.10% | 14 +/− 0 | 24 +/− 0 |
| NaHA 1.6%-EG68(0) 0.25% | — | — |
| NaHA 1.6%-EG68(0) 0.10% | — | 29 +/− 0 |
| NaHA 1.6%-Es 0.25% | 20 +/− 4 | 27 +/− 4 |
| NaHA 1.6%--Es 0.10% | 24 +/− 1 | 29 +/− 2 |
| Visthesia ® solution (Zeiss) | Not ejected | Not ejected |

The results show that the presence of slippery viscoelastic solution (solution containing sodium hyaluronate or hydroxypropyl methylcellulose combined with a polymer of the polyether urethane or also polyether polyester urethane type) during injection allows intraocular lenses, having a hydrophobic, hydrophilic nature or also hydrophilic with a hydrophobic surface, to be injected through a small-diameter tip, with injection forces less than 30 N. These tests were carried out with cartridges without any treatment promoting the ejection of the intraocular lens. On this same device, the ejection of an intraocular lens, even having low dioptre units, by means of a solution containing only sodium hyaluronate or hydroxypropyl methylcellulose (without slippery polymer) is not possible.

The values for the injection force measured in the presence of the viscoelastic solutions used according to the invention are comparable to those measured for injector tips coated with a slippery polymer and using a standard viscoelastic solution.

By way of comparison, the force necessary to inject a hydrophilic implant of the AcriLISA® type of 28 dioptres by means of a Viscoject cartridge of 2 mm diameter coated with a slippery polymer is 13 N+/−1.

The invention claimed is:

1. An aqueous viscoelastic solution comprising:
at least one polymer selected from hyaluronic acid and salts thereof, and cellulosic derivatives and salts thereof, and
at least one water-soluble polymer of the polyether polyurethane or polyether polyester urethane type,
said viscoelastic solution having a viscosity comprised between 10 and 7000 Pa·s, and wherein said water-soluble polymer of the polyether polyurethane or polyether polyester urethane type does not have a terminal or pendant fatty acid chain comprising at least 10 carbon atoms.

2. The viscoelastic solution according to claim 1, in which the hyaluronic acid has a weight average molecular weight comprised between 1.5 MDa and 5 MDa.

3. The viscoelastic solution according to claim 1, wherein the hyaluronic acid has a weight average molecular weight comprised between 0.5 MDa and 1.5 MDa.

4. The viscoelastic solution according to claim 1, in which the hyaluronic acid is in the form of sodium or potassium hyaluronate.

5. The viscoelastic solution according to claim 1, in which said cellulosic derivative is hydroxypropyl methylcellulose or one of the salts thereof.

6. The viscoelastic solution according to claim 1, in which the content of polymer selected from hyaluronic acid and salts thereof, and cellulosic derivatives and salts thereof, is comprised between 0.5 and 3%, expressed in weight/volume.

7. The viscoelastic solution according to claim 1, in which the water-soluble polymer of the polyether polyurethane type is an ethylene oxide and propylene oxide block copolymer.

8. The viscoelastic solution according to claim 7, in which the water-soluble polymer of the polyether polyurethane type is a branched ethylene oxide and propylene oxide block copolymer comprising urethane, allophanate and urea bridges.

9. The viscoelastic solution according to claim 7, in which said water-soluble polymer of the polyether polyurethane type has a weight average molecular weight greater than or equal to 20 KDa.

10. The viscoelastic solution according to claim 1, in which the water-soluble polymer of the polyether polyester urethane type is a branched polyether and polyester copolymer comprising urethane, allophanate and urea bridges.

11. The viscoelastic solution according to claim 10, in which said water-soluble polymer of the polyether polyester urethane type has a weight average molecular weight greater than or equal to 20 KDa.

12. The viscoelastic solution according to claim 1, in which the content of water-soluble polymer of the polyether polyurethane or polyether polyester urethane type in the aqueous viscoelastic solution is comprised between 0.10 and 0.5%, expressed as weight/volume.

13. A method for injection of an intraocular implant into an eye comprising: injecting an intraocular implant into an eye with a device intended for injection, wherein said device contains an aqueous viscoelastic solution comprising:
at least one polymer selected from hyaluronic acid and salts thereof, and cellulosic derivatives and salts thereof, and
at least one water-soluble polymer of the polyether polyurethane or polyether polyester urethane type,
said viscoelastic solution having a viscosity comprised between 10 and 7000 Pa·s, and wherein said water-soluble polymer of the polyether polyurethane or polyether polyester urethane type does not have a terminal or pendant fatty acid chain comprising at least 10 carbon atoms.

14. The method according to claim 13, wherein said device comprises an injection body, a tip, a loading cartridge and an injection piston.

15. The method according to claim 13, wherein said aqueous viscoelastic solution makes it possible to reduce the force to be exerted on the piston of said device.

16. The method according to claim 14, wherein said viscoelastic solution is introduced into said loading cartridge before, or simultaneously with, the loading of the intraocular implant.

17. The method according to claim 13, wherein said viscoelastic solution makes it possible to apply an injection force less than 30 N, on the piston of an injection device equipped with a tip having an aperture of diameter equal to or less than 2.6 mm.

18. A device for the injection of an intraocular implant, comprising an injection body, a loading cartridge and an injection piston, wherein the loading cartridge contains a viscoelastic solution of claim 1.

19. The viscoelastic solution according to claim 1, further comprising a hydrophilic or hydrophobic intraocular implant.

* * * * *